United States Patent [19]

Sloan

[11] 3,977,084
[45] Aug. 31, 1976

[54] DENTAL HYGIENIC DEVICE

[75] Inventor: Robert I. Sloan, West Vancouver, Canada

[73] Assignee: TSSET Scientific and Pharmaceutical Limited, Canada

[22] Filed: Aug. 26, 1974

[21] Appl. No.: 500,376

[52] U.S. Cl. ............................................. 32/59
[51] Int. Cl.² ..................................... A61C 3/06
[58] Field of Search........................... 32/57, 58, 59

[56] References Cited
UNITED STATES PATENTS

| | | | |
|---|---|---|---|
| 1,720,017 | 7/1929 | Touchstone | 32/59 |
| 2,789,352 | 4/1957 | Wiseman | 32/58 |
| 3,461,563 | 8/1969 | Nelson | 32/59 |
| 3,675,330 | 7/1972 | Drapen | 32/59 |
| 3,757,419 | 9/1973 | Hopkins | 32/59 |
| 3,775,849 | 12/1973 | Condon | 32/59 |
| 3,858,368 | 1/1975 | Cocherell | 32/59 |

Primary Examiner—Robert Peshock
Attorney, Agent, or Firm—Howard D. Gordon

[57] ABSTRACT

A dental hygienic device including a unique prophylactic cup for removal of dental plaque and/or polishing teeth. The generally bell shaped prophylactic cup includes an inner generally concave working surface for engagement of the tooth surfaces. The inner surface will form an outwardly flaired lip to conform with and adapt to the irregular surfaces of teeth and for limited, controlled entry into the gingival crevice. The inner working surface therefor abrasive members which may vary according to the distance from the outer lip of the inner surface and the outer surface of the cup includes a member which will limit entry of the outer lip of the cup into the gingival crevice.

11 Claims, 19 Drawing Figures

DENTAL HYGIENIC DEVICE

BACKGROUND OF THE INVENTION

1. Field of the Invention

This invention relates to dental hygienic devices and more particularly to movable prophylactic cups for the removal of dental plaque, massage of the free gingiva and/or polishing of tooth surfaces.

2. Description of the Prior Art

There are two major dental diseases, the occurrences of which are directly related to the effectiveness or quality of personal dental hygiene. Both of these diseases are believed by many dental experts to be related to the formation of plaque on tooth surfaces and the gingiva and the ability of the individual to effectively remove all of the plaque through normal daily tooth care. It is believed plaque begins as a sticky substance released by the salivary glands in the oral cavity. The substance readily adheres to the tooth surfaces and bacteria commonly found in the oral cavity become attached to and embedded in the coating on the teeth. The process through which the plaque is deposited in continual, and though exposed tooth surfaces are completely cleaned of dental plaque, evidence has shown that new plaque is deposited usually within 24 hours or sooner. Dental plaque and the bacteria associated with plaque are commonly accepted as being the basic causative elements of the two primary dental diseases; dental caries and periodontal disease.

Periodontal disease is generally believed to be caused by plaque deposits along the gum or gingival line. This area includes not only directly exposed enamel tooth surfaces, but also the gingival crevices formed between the free gingiva and/or the enamel and cementum surfaces of the teeth. The gingival crevice is an area which is virtually inaccessible by toothbrush. Plaque deposits that form at the crevice interface their bacteria with gingival tissues and may cause irritation. If the deposits are not removed, severe gingival irritation, inflamation and bleeding occurs and bone resorption can begin, resulting in ultimate tooth loss.

From the foregoing, it can be seen that to suppress or, if possible, prevent periodontal disease, efficient daily cleaning is necessary. This includes the removal of food particles and plaque from all areas of the dental structure preferably at least once a day. Thorough daily cleaning is required to reduce the high incidence of periodontal disease occurring in individuals who, by present standards, take or attempt to take good daily care of their teeth. It is toward this end that the personal dental hygiene instrument of the present invention is intended. The instrument is designed to complement the benefits derived by daily flossing by providing more efficient and thorough removal of plaque from tooth surfaces. In addition, the instrument may provide for thorough massage of gingival tissues as an adjunct to complete dental care.

Prior art dental hygienic devices have included prophylactic cups such as are disclosed in U.S. Pat. Nos. 3,599,333 and 3,621,577. These cups include a plurality of ribs for retaining an abrasive material. While such a cup will enter the gingival crevice to remove the plaque from the dentum the cups have no means limiting insertion into the crevice and no means to limit the abrasive action on the relatively softer cementum. The prior art devices are thus most suited for periodic use by trained personnel such as dentists and/or dental hygienists and are not intended for home use by untrained personnel.

SUMMARY OF THE INVENTION

In accordance with the present invention, the drawbacks of the prior art have been overcome to the extent that a dental hygienic device suitable for daily use by an untrained user to remove dental plaque has been provided. The above is accomplished by utilizing a movable prophylactic cup of generally bell shape having a concave, inner working surface intended to flair outwardly upon contact with a tooth surface to conform with and adapt to the irregular surfaces of the teeth. The outwardly flaired inner surface will define a radially outer lip capable of insertion into the gingival crevice while a member on the outer surface of the cup will limit the extent of insertion into the crevice by the lip. The inner surface carries abrasion members which are less abrasive or at least less in number closer to the outer circumference of the lip.

The cup is preferably rotated and may carry an eccentric projection on the outer surface thereof to apply compressive and relaxing massage action to the gums. The cup may also include fluid passages therein to convey a dentifrice or the like to the tooth surface, both above and below the gingiva line, at the time of plaque removal when the dentifrice will be most effective, to flush the gingival crevice and also to bring the non-diluted dentifrice into direct contact with that portion of the tooth forming an inner wall of the gingival crevice.

Accordingly, it is an object of this invention to provide a new and improved dental hygienic device suitable for use by relatively untrained personnel for the removal of dental plaque.

Another object of the present invention is to provide a new and improved dental hygiene device including a movable dental prophylactic cup which will flair outwardly to define a lip for controlled insertion into the gingival crevice and which will provide only limited abrasive action to that portion of the tooth forming a portion of the gingival crevice which is often wholly or partially cementum or dentum.

A further object of the present invention is to provide a dental hygienic device of the type described which will also apply a massaging effective to the gum tissue.

These and other objects and advantages of the present invention will become apparent from a reading of the following detailed description taken in connection with the attached drawings.

DESCRIPTION OF THE PREFERRED EMBODIMENT

Figure 1:
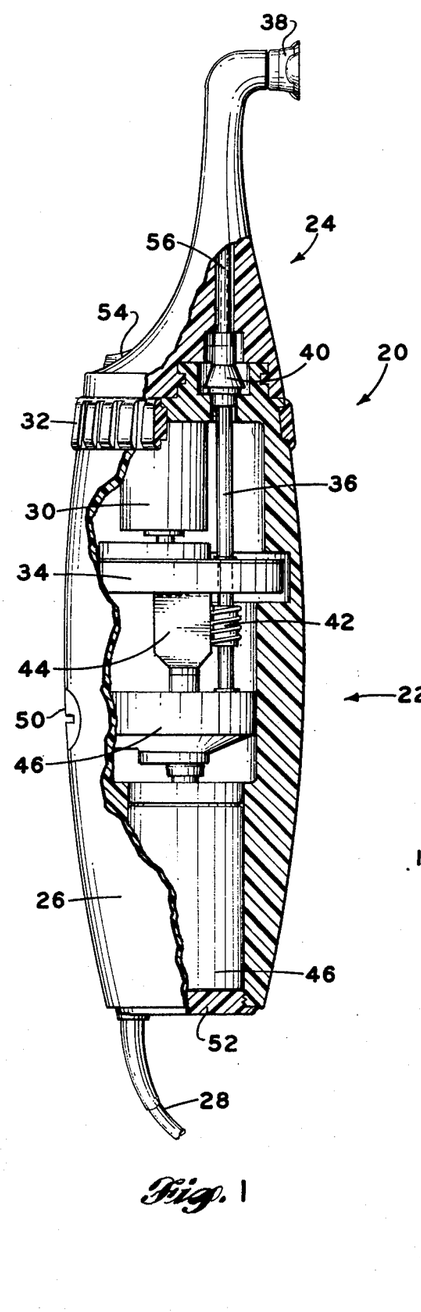
FIG. 1 is a partially cutaway side view of a hand-held dental hygiene instrument of this invention employing a unique prophylatic cup which functions to remove dental plaque and provide gingiva massage.

FIG. 1 illustrates a hand-held externally powered dental hygiene instrument 20 utilizing the prophylatic cup of the present invention. The device is designed for daily home care of teeth and gums and performs two specific functions; it removes plaque accumulations from enamel and exposed cementum surfaces of the teeth and simultaneously performs a unique gum or gingiva conditioning function. The device may also be utilized to polish teeth. It is believed that polished teeth will be more attractive and will also be smoother to better resist the re-deposit of dental plaque. In performing these functions, the device can also deliver fluorides and other anti-plaque and anti-caries agents to all of the dental surfaces and directly into the freshly cleaned tooth and also may be directed to act as a flushing agent. The instrument is comprised of two basic functional units: the power and dentifrice supply assembly 22, and the removable hygienic head assembly 24. The power and dentifrice supply assembly 22, as the nomenclature implies, provides motive power for the instrument and includes a replenishable supply of dentifrice and an automatic, controllable delivering means. The assembly is housed in a case 26 typically molded of high-impact plastic or metal plated plastic which functions to contain, protect and support internal working components. The case 26 is molded in such a manner that its external contours accommodate the grip of the average user with attention to the position in which the device is held for use. In this preferred embodiment, the assembly receives house current (110 volt) through an electrical cord 28 or may be battery operated to power motor 30 which is controlled by switch 32 incorporated into a rotatable ring about the case 26. The motor 30 via gear train 34 imparts rotational drive to the output drive shaft 36. The shaft 36 in turn transmits the rotation to the prophylatic cup 38 on the detachable hygienic head assembly 24 through a frictional drive coupling 40. Rotation of the output drive shaft 36 is also coupled through a gear arrangement 42 to a pump 44 which draws dentifrice from the replaceable supply cartridge 46 through supply valve 48 and conveys it to the hollow core of output drive shaft 36. The drive shaft 36 performs the dual function of dentifrice supply conduit. Dentifrice pumped through the hollow output shaft 36 is supplied to the hygienic head assembly 24 through the liquid-tight frictional drive coupling 40. A screw adjustment 50 on the side of the case 26 provides for adjustment of dentifrice flow through shaft 36 to the hygienic head 24. Screw cap 52 retains the dentifrice cartridge 46 in the proper position in the case 26. It is understood that although rotational movement of cup 38 is preferred, any motion will provide the required movement between the cup and the tooth surface and it is also understood that motion may be manually applied.

Since the head assembly 24 as illustrated in FIG. 1 is inserted into the user's mouth, the assembly is detachable for obvious hygienic reasons. The unit would normally be purchased with a separate color-coded hygienic head assembly 24 for each individual intending to use the unit. Each head assembly 24 is molded of high-impact plastic with outside head contours designed to facilitate positioning of the instrument for application of the prophylactic cup 38 to essentially all dental surfaces. The head assembly includes a spring-loaded latch mechanism providing for snap-on attachment of the head assembly to the power and dentifrice supply assembly 22. A push-button type release catch 54 provides for fingertip control of the latch mechanism. A hollow upper drive shaft segment 56 is rotatably mounted in the head assembly 24 and includes the female portion of the friction drive coupling 40. When the head assembly 24 is snapped into place on the power and dentifrice supply assembly 22, the female drive coupling fitting mates with the male fitting on the lower assembly forming a positive fluid-tight coupling. In this manner, rotational drive power is coupled to the head from output drive shaft 36. In addition, dentifrice from the supply in lower assembly 22 is conducted through the drive shaft 36 and drive coupling 40 to the head assembly 24. Dentifrice pumped to the head assembly through coupling 40 in this manner is channeled to the prophylactic cup 38 through the hollow core of shaft segment 56.

Figures 2, 3:
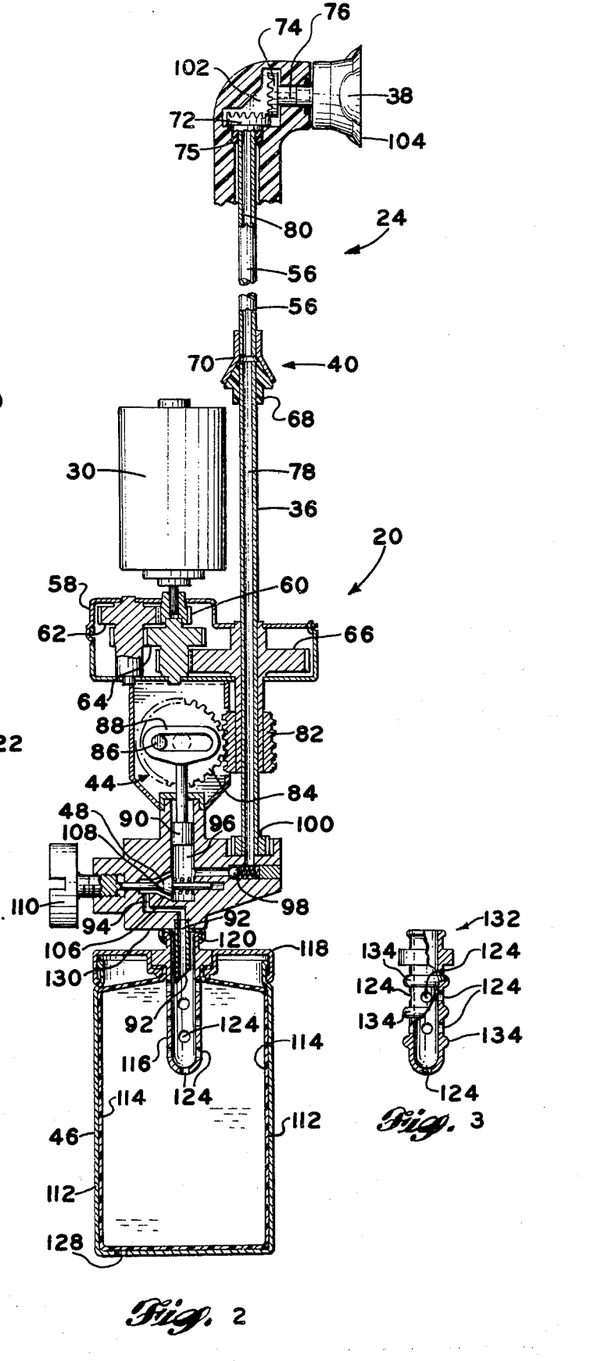
FIG. 2 is a partially cross-sectioned diagrammatic view illustrating the working components of the device shown in FIG. 1.
FIG. 3 is a partially cutaway view of an alternate embodiment of a dentifrice delivery tube employed in the embodiment of FIG. 2.

The inner workings of the invention as contained in the case 26 described in FIG. 1 are depicted in more detail in FIG. 2. In the preferred embodiment the device 20 is powered by an electric motor 30 driven from a 110 volt, 60 cycle source via an integrally or removably attached electrical cord 28. The motor 30 preferably rotates the hollow output drive shaft 36 at approximately 800 rpm through a reduction gear box 58. A reduction of approximately 8 to 1 between the motor 30 and the output drive shaft 36 is achieved through the gear chain consisting of spur gear 60, idler 62, pinion 64 and output gear 66. As the output shaft 36 is driven, the rotational movement is transmitted to the upper shaft segment 56 in the hygienic head 24 through the frictional drive coupling 40. With the hygienic head 24 snapped into place as previously described, the male and female elements 68 and 70 of the coupling 40 form a positive liquid-tight frictional interface. Rotational movement coupled to shaft segment 56 in the hygienic head 24 rotates the prophylactic cup 38 through the right angle drive formed by crown gears 72 and 74 and output shaft 76.

The hollow output drive shaft 36 and the upper shaft segment 56 in the hygienic head 24 not only provide the rotational drive for the prophylactic cup 38, but also function to convey dentifrice to the cup 38 through the interior channels 78 and 80 of the shafts. The dentifrice is drawn from the replaceable cartridge 46 through the operation of a reciprocating piston pump 44 which is driven by the rotation of the output drive shaft 36 via a slotted yoke drive. Rotation of worm gear 82 on the shaft 36 causes rotation of worm wheel 84 upon which a drive pin 86 is eccentrically mounted. The drive pin 86 engages a slotted yoke 88 which is an integral part of piston 90. Action of the drive pin 86 in the slot of yoke 88 as worm wheel 84 rotates causes piston 90 to reciprocate. On the piston upstroke toward the worm wheel, dentifrice is drawn from the cartridge 46 through puncture probe 92 and orifice 94 through supply valve 48 into cylinder 96. On the downstroke, the piston 90 compresses the dentifrice in the cylinder 96 generating sufficient pressure to overcome spring-loaded ball valve 98. The dentifrice is forced through the valve 98 past pressure-sealed shaft bearing 100 and into the rotating output shaft 36. The dentifrice passes through frictional drive coupling 40 and upper shaft segment 56 into the cavity 102 in the head assembly 24 which houses the right-angle-drive crown gears 72 and 74. The cavity 102 is sealed by O-ring 75. The abrasive-free dentifrice from the cavity through the hollow center of output shaft 76 and onto the functional surfaces 104 of the prophylactic cup 38. Flow of the dentifrice to the cup can be regulated through the adjustment of the supply valve 48. The valve 48 is spring-loaded against its seat 106 and the clearance between the valve block 108 and the seat 106 can be varied by rotating adjustment screw 110 thereby regulating dentifrice flow.

The replaceable dentifrice cartridge 46 consists basically of a metal, plastic or cardboard outer container shell 112 which houses a sealed polyethylene bladder 114 containing the dentifrice. A delivery tube 116 is mounted along the axis of the cartridge 46 inside the bladder. The bladder 114 is attached along the interface between the cap 118 and delivery tube 116 in such a manner that a fluid-tight seal is formed. The external end of the tube 116 is terminated in a flared peripheral lip 120 over which a tightly fitting rubber diaphragm 122 is installed to seal the end of the tube 116. Internally, the delivery tube 116 is perforated by symmetrically spaced delivery holes 124 along its length. A vent hole 128 in the end of the cartridge 46 allows the ambient air to reach the outside of the bladder 114 thereby assuring that internal cartridge pressure is equalized as dentifrice is pumped out and the bladder 114 contracts.

The outer case of the dental care device is so designed that a replacement dentifrice cartridge 46 is introduced into its guide channel in the case and seated against its stops, probe 92 punctures the rubber diaphragm 122 on the end of the delivery tube 116. The diaphragm 122 then seats against the supply valve housing 130 to form a fluid-tight seal and probe 92 is positioned inside the delivery tube 116. Installing the retaining cap 52 on the dentifrice cartridge compartment on the case as shown in FIG. 1 holds the cartridge in this delivery position. Dentifrice is sealed in the bladder 114 inside the cartridge 46 under a slight positive pressure. Thus, when the cartridge is installed in the device and probe 92 punctures diaphragm 122, the internal positive pressure causes an initial surge of dentifrice through the probe 92 and supply valve 48 to cylinder 96 to assure that pump 44 is primed. The bladder-type delivery cartridge 46 is used specifically to insure uninterrupted flow of dentifrice to the pump 44 during powered operation regardless of the attitude at which the device is held by the user. As the pump 44 draws dentifrice from the cartridge 46, the bladder 114 contracts.

FIG. 3 describes an alternate embodiment of the dentifrice cartridge delivery tube. The alternate 132 may have a length up to and including the full length of the cartridge. Annular ridges 134 are located between the successive rings of delivery holes 124 to assure continued flow of dentifrice until the cartridge is completely emptied. As the dentifrice is exhausted from the cartridge, and the polyethylene bladder 114 within the cartridge, FIG. 2, contracts against the delivery tube 132, FIG. 3, the ridges 134 prevent the bladder from entirely sealing the delivery holes 124.

Figure 4:
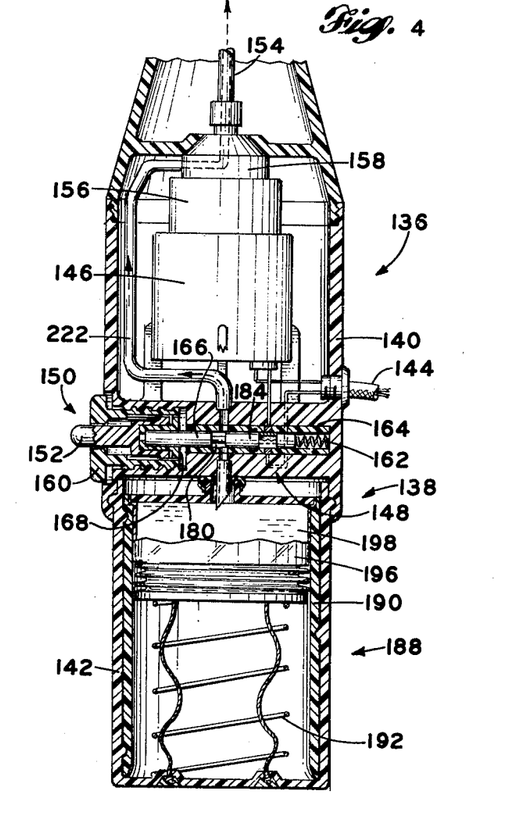
FIG. 4 is a partially cross-section diagram of an embodiment of the hand-held dental hygiene instrument of the present invention.
Figure 4A:
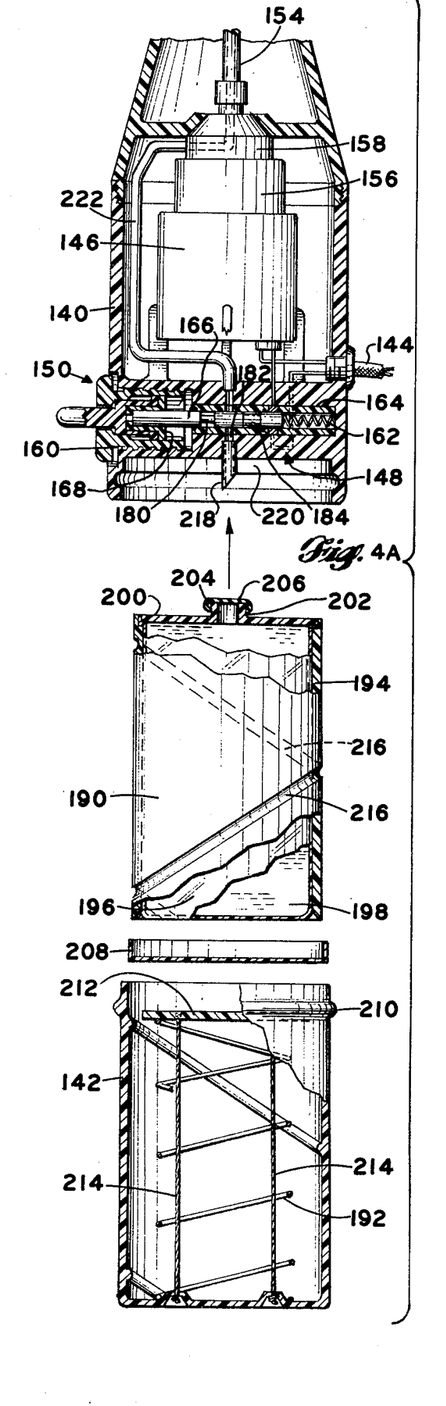
FIG. 4A is a partially exploded view of the instrument of FIG. 4.

FIGS. 4 and 4A illustrates an alternate embodiment of the hand-held, externally powered dental hygiene instrument. The instrument 136 is comprised of two basic functional units: the power and dentifrice supply assembly 138, and a removable hygienic head assembly not shown in the FIGURES. The power and dentifrice supply assembly 138 provides motive power for the instrument and includes a replenishable supply of dentifrice and a delivering means. The assembly is housed in a two-part case 140 and 142, typically made of molded, high-impact plastic which functions to contain, protect and support internal working components. as with the preferred embodiment, the case is molded in such a manner that external contours accommodate the grip of the average user with attention to the attitude at which the device is held for use. The instrument receives house current (110 volt) through an electrical cord 144 to power a motor 146 which is controlled by a switch 148. The switch maybe operated by a simply "Hart" mechanism 150 similar to the type of mechanism commonly used in ball point pens to extend and retract the point or may be operated by other suitable mechanism. In this application, the push button 152 of the spring-loaded Hart mechanism 150 is pressed to actuate the switch 148 and energize the motor 146, and then is pressed again to release the mechanism and open the switch, thereby de-energizing the motor. When energized, the motor 146 imparts rotational drive to the hollow output shaft 154 via a gear arrangement 156 and a dentifrice manifold 156. The shaft 154 transmits rotation to the prophylactic device of the hygienic head.

Figure 5:
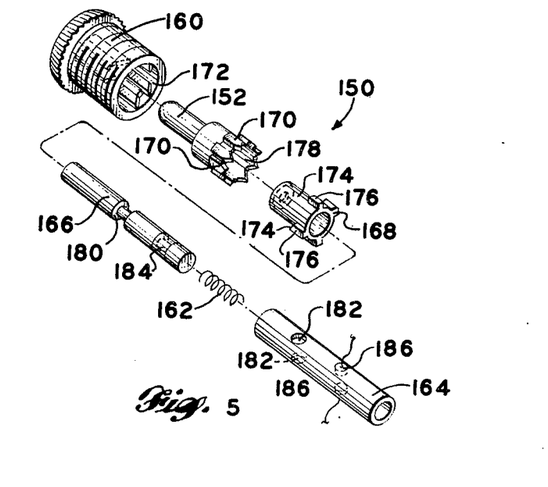
FIG. 5 is an exploded view of the control mechanism of the instrument of FIGS. 4 and 4A.
Figure 6:
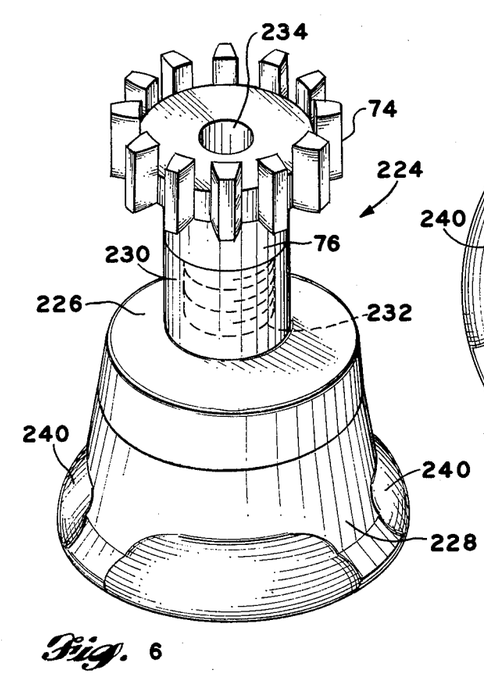
FIG. 6 is an isometric view of the preferred embodiment of the prophylactic cup of this invention.
Figure 7:
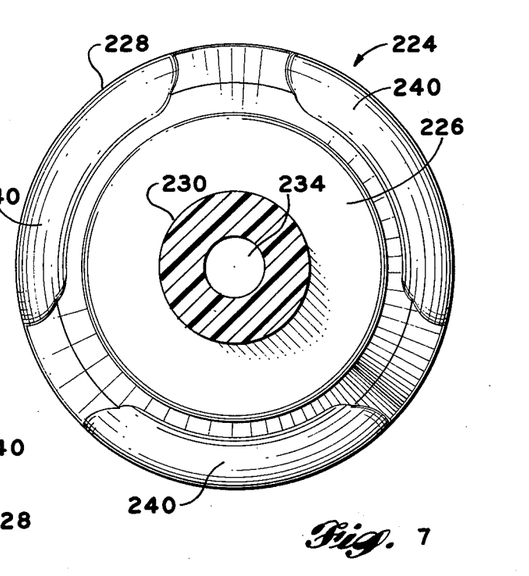
FIG. 7 is a plan view of the prophylactic cup illustrated in FIG. 6 taken along the section lines shown in FIG. 9.

The Hart mechanism 150, in addition to providing on-off switch control, also provides control of the dentifrice flow valve. Therefore, when the mechanism is activated and the switch closes and energizes the motor, the flow valve is also opened. FIG. 4A illustrates the mechanism in the de-activated state; FIG. 4 the activated or on state; and FIG. 5 provides an exploded isometric view of the Hart mechanism elements. The threaded sleeve 160 is integrally screwed into the case 140 of the instrument and serves to hold captive all of the other elements of the mechanism under varying degrees of spring tension. The spring 162 is housed in a sleeve 164 and bears against the case on one end and the slider 166 on the other end. The succession of mutually interfacing elements, including the slider 166, flanged sleeve 168 and push button 152 are effectively spring loaded since the push button bears against retentive surfaces inside the threaded sleeve 160.

The raised wedge-shaped splines 170 on the push button 152 coincide with splined grooves 172 inside the threaded sleeve 160 such that the push button can slide longitudinally within the threaded sleeve under spring tension, though it can not be turned or displaced radially. Thus, when the push button 152 is pressed in, the points of the wedge-shaped splines 170 on the push button are aligned to contact the beveled ends 174 of the flanges 176 on the flanged sleeve 168. This contact slideably displaces the flanged sleeve radially ⅛ of a turn until the flanges 176 seat in the notches 178 between the push button splines 170. Then as the push button 152 is released under spring tension, the push button holds the flanged sleeve 168 in alignment for one of two modes of operation.

As the push button 152 is released to revert the instrument to a de-activated state as shown in FIG. 4A, the flanges 176 on the flanged sleeve 168 are held in alignment by the push button with the grooves 172 inside the threaded sleeve 160. Thus, as the push button is released, the flanged sleeve is allowed to be completely compressed with the push button inside the threaded sleeve under reduced spring tension. In this mode, the spring 162 remains under only enough compression to keep the slider 166 mated with the flanged sleeve 168. Thus, the slider is displaced enough longitudinally to misalign the valve opening 180 on the slider 166 and the flow through orifice 182 in the sleeve 164, thereby effectively closing the valve and stopping flow. In addition, the metal contact ring 184 on the slider 166 is displaced from the contacts 186 in the sleeve thereby opening the motor power circuit. Thus, the instrument is completely de-activated.

To activate the instrument, the push button 152 is again pressed, displacing the flanged sleeve 168 and slider 166 longitudinally against the spring 162. The displacement aligns the valve opening 180 in the slider with the orifices 182 in the sleeve allowing dentifrice flow, and also aligns the metal contact ring 184 with the contacts 186 in the sleeve thereby closing the switch 148 and energizing the motor 146. The mechanism is locked in this configuration through the operation of the push button 152 and flanged sleeve 168. As the push button is pressed energize the device, the push button splines 170 displace the flanged sleeve 168 radially ⅛ turn. Thus, positioned the flanges 176 are aligned with the stops inside the threaded sleeve 160 which prevent the flanged sleeve from receding with the push button element when it is released. Thus, the Hart mechanism maintains the device in an energized state until the push button is again depressed to rotate the flanged sleeve ⅛ turn and de-energize the device as previously described.

The dentifrice supply mechanism 188 occupies the lower portion of the dental hygiene device illustrated in FIGS. 4 and 4A. In this embodiment a replaceable, sealed cartridge 190 is used which is mechanically pressurized by a spring 192 in the lower case 142. The replaceable dentifrice cartridge 190 consists basically of a metal plastic or cardboard outer container shell 194 which houses a sealed polyethylene bladder 196 containing dentifrice 198. The bladder 196 is attached to the cartridge along the interface between the cap 200 and the outer container shell 194 such that a fluid-tight seal is formed. A tube segment 202 situated in the center of the end cap 200 is terminated in a flared, peripheral lip 204 over which a tightly fitting rubber diaphragm 206 is installed to seal the cartridge 190. On the lower end of the cartridge 190 the internal bladder 196 is protected by a disposable end cap 208.

the outer case of the dental care device is designed such that the lower portion 142 forms a dentifrice cartridge housing which is removable from the device via a screw-on or snap fitting 210. The lower case 142 consist of a cylindrical cup containing the pressure spring 192. A piston 212 is secured to the upper end of the spring 192 inside the cup. Snubber springs 214 secured to the bottom of the case 142 and to the piston 212, limit the upward throw of the piston and effectively retain the spring.

To insert the dentifrice cartridge 190 into the instrument, the lower case 142 which forms the cartridge housing is separated from the upper case 140. The disposable end cap 208 is removed from the cartridge 190 and the cartridge is then seated on the piston 212 and is pressed into the case 142 to compress the spring 192. Note that an exaggerated screw thread arrangement 216 between the lower case 142 and the cartridge container shell 190 requires that the cartridge be turned into the lower case. The exaggerated threading serves to prevent the cartridge from flying out of the housing under spring pressure.

With the cartridge 190 installed in the lower case 142, thereby fully compressing spring 192, the assembly is ready to be installed on the main body of the device. The tip of probe 218 is made to pierce the diaphragm 206 on the cartridge 190 to initiate installation. At the same time, the lower case 142 containing the cartridge snaps or screws into place on the upper case 140, and the diaphragm 206 seats against the lower surface 220 of the upper case 140 to form a fluid-tight seal. The spring 192 in the lower case 142 being compressed applies pressure to the bladder 196 via the piston 212. Thus, the cartridge bladder is effectively pressurized causing dentifrice to be forced through the probe 218 to the orifice valve formed by the valve opening 180 in the slider 166 and the orifices 182 in the sleeve 164 of the Hart mechanism 150. As previously described, the valve operates in conjunction with the motor on-off switch 148 as actuated by the Hart mechanism push button 152. When the push button 152 is pressed, the motor 146 is energized and the valve is opened. With the valve open as shown in FIG. 4, dentifrice 198 from the spring-pressurized cartridge 190 is forced through the valve and a supply tube 222 to the dentifrice manifold 158. The manifold conducts the dentifrice into the hollow core of the rotating output shaft 154 which in turn conveys it to the operating head of the device. Pressing the Hart mechanism push button 152 a second time opens switch 148 shutting off the motor 146 and closing the valve by displacing the opening 180 in slider 166 from alignment with the orifices 182 in sleeve 164.

The pressure spring 192 maintains a constant pressure on the bladder 196 throughout the life of the cartridge 190 thereby assuring a constant flow of dentifrice through the probe 218 to the valve. As the dentifrice is used up, the bladder 196 under pressure from the spring 192 folds on itself in a random accordion fashion as piston 212 is pressed upward toward the probe 218. When dentifrice in the bladder is exhausted, replacement of the cartridge is accomplished simply by unsnapping the lower case 142, removing the old cartridge 190 and installing a fresh cartridge as previously described. It is appreciated that other cartridge configurations are possible within the scope of the present invention.

The prophylactic cup 224 may be replaceable, as illustrated in FIGS. 6 through 11, is that portion of the present invention which physically cleans the dental surfaces and massages the gingiva and may also polish the teeth. It is basically a molded, flexible rubber or plastic cup nominally 5mm. in diameter mounted on a relatively firm base such as a metal or plastic shaft or the like by which the cup is moved preferably rotated to impart scrubbing and massaging action. Although true rotation is preferred, any motion which will provide the relative movement between cup and tooth is adequate. The actual shape and size of the cup can vary widely to emphasize particular scrubbing or massaging and/or polishing characteristics or effects. The major cup design stipulation is that the inside scrubbing areas be adaptable to the variety of dental surfaces to be serviced, and at the same time be able to extend into the gingival crevice in such a manner that the outside surface of the cup will properly and simultaneously engage and flex the free gingiva.

In the preferred embodiment, the prophylactic cup 224 is fabricated in a double injection molding process of two types of plastic. The base portion 226, upon which the cup 228 is mounted and which adapts to the drive elements of the hygienic head of the instrument, is injection molded in a primary stage of relatively hard nylon material. The base 226 includes a shaft segment 230 which is internally threaded 232 to facilitate connecting to the crown drive gear 74 (reference FIG. 2) via the threading on the shaft 76 of the hygienic head. The cup 228 itself is molded directly onto the base 226 in a second injection molding stage of pliable vinyl plastic. Both the base and cup portions are molded about a common central channel 234 which effectively forms an extension of the hollow channel 234 in shaft 76 of the hygienic head. The channel provides for delivery of dentifrice directly to the dental surface during use of the instrument. The dentifrice not only may function as a partially antiseptic cleaning agent, but also may lubricate the rotating scrubbing surfaces of the cup on the dental surface, impart pleasant taste, feel, etc., or act as a flushing agent.

The cup portion 228 of the prophylactic cup 224 as illustrated in FIGS. 6 through 10, is molded in a roughly truncated section directly onto the base portion 226 in a second injection molding stage. The cup is molded in such a manner that a peripheral cavity 238 in the base portion is filled with the vinyl plastic material of which the cup is formed thereby firmly anchoring the cup 228 to the base 226. The central dentifrice channel 234 molded into the cup precisely coincides with the channel molded into the base portion. The cup is sculptured externally to form raised or thickened portions or crowns 240 which function to massage the gingiva by compressing the gingiva and then allowing the gingiva to relax.

Figure 10:
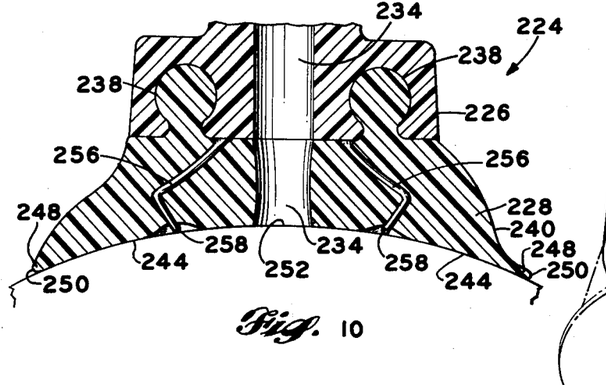
FIG. 10 is a partial cross-sectional view of the cup illustrated in FIG. 6 as it would appear compressed against a dental surface with its features in operating attitude.

The inside of the flexible cup is hollowed in a roughly bell-shaped cavity 242 described by a conically inclined interior surface 244. The lower interior surface segment 446 forms the inside face of a highly flexible peripheral flange 248 about the lower extremity of the cup. The configuration of the cavity 242 is such that the thickness of the flange 248 varies and subsequently its flexibility varies from the lower highly defined rim 250 toward the base portion 226. When the cup is compressed against the tooth such that the interior surface actively and fully engages the tooth surface 252, as shown in FIG. 10, the cup 224 is distorted to one of its optimum operating shape. The dentifrice channel opening 254 in the center of the interior surface 244 enhances the overall flexibility of the cup enabling it to conform to a variety of contoured surfaces.

Figures 8, 9:
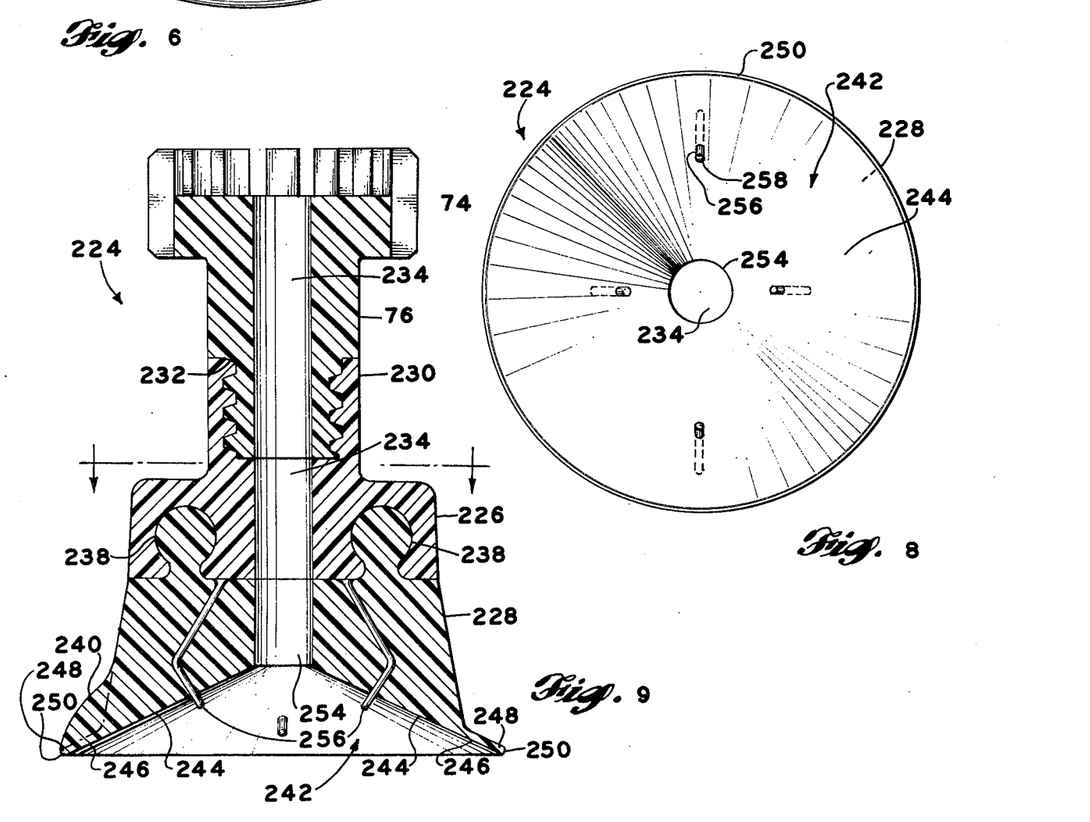
FIG. 8 is a plan view of the working face of the prophylactic cup illustrated to FIG. 6.
FIG. 9 is a cross-sectional view of the cup illustrated in FIG. 6.
Figure 9A:
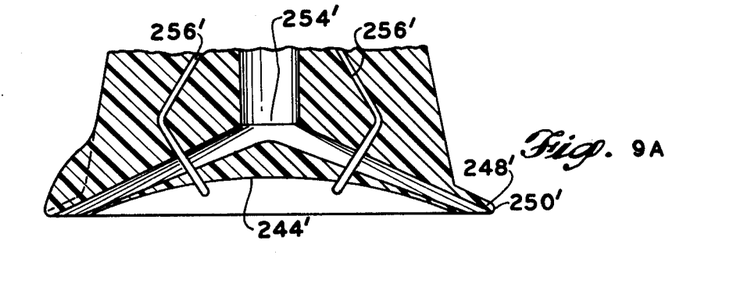
FIG. 9A is a cross-sectional view of an alternate form of the prophylactic cup.
Figure 11:
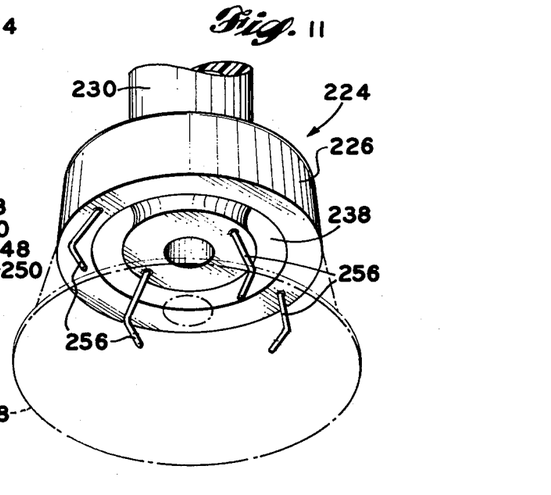
FIG. 11 is a partial isometric view of the molded base portion of the cup illustrated in FIG. 6.

Since the interior surfaces 244 of the cavity 242 in the cup perform the actual scrubbing and/or polishing function and interface with the enamel coating on the tooth crown and exposed parts of the cementum of the tooth root, particular attention is given to the texture and configuration of the interior surfaces. In the preferred embodiment of the invention, the interior surfaces 244 include relatively stiff nodules or bristles 256 which function to engage the dental surfaces and to remove plaque deposits. The bristles are cast as integral parts of the base portion 226 of the cup assembly, as shown in FIGS. 9, 10 and 11, during the initial injection molding stage. The relatively hard, durable nylon of which the base is cast yields bristles ideally suited to this application. During the second injection molding stage, the pliable cup 228 is cast onto the base 226, as previously described, and the bristles 256 are encapsulated in the cup molding except for the tips 258 which protrude from the interior working surfaces 244 of the cup. The elements in addition to being naturally flexible, are cast in an angular configuration to ensure proper attitude during use. When the cup 228 is pressed against the tooth surface 252 and distorted to its optimum operating shape, the angular shape of the bristles 256 cause the tips 258 to substantially perpendicularly intersect the surface. This arrangement ensures optimum scrubbing action by the abrasive tips. It should also be noted that the alternate bristles on the base casting are spaced at different distances from the rotational axis of the cup. This feature provides for alternately opposing bristles to engage different areas of the tooth surface relative to the rotational axis as the cup rotates.

FIG. 10 illustrates a prophylactic cup 224 of the type just described employing bristles of an angular configuration. The rotation cup 228 is pressed against the tooth surface 252 causing the flexible cup to "bell out" or flair to a distorted shape which presses the entire working surface 244 of the cup against the dental surface. The angularly configured bristles 256, being embedded in the cup, flex as the cup bells out. The flexing allows the abrasive tips 258 of the bristles to engage the tooth surface at an essentially perpendicular attitude for optimum scrubbing action as the cup rotates. It is obvious that many bristle or nodule or protrusion configurations are possible to meet the multiplicity of abrasive requirements. Though four bristles are illustrated in the preferred embodiment, two, three or a number more may be employed. It is also possible that separate synthetic or natural fibers or bristles may be cast into the base casting with subsequent embedding in the secondary cup molding, or bristles may be cast only in the cup molding for anchoring. It is also noted that various arrangements of separate plaque removing and separate polishing abrasive means may be utilized.

Figure 14:
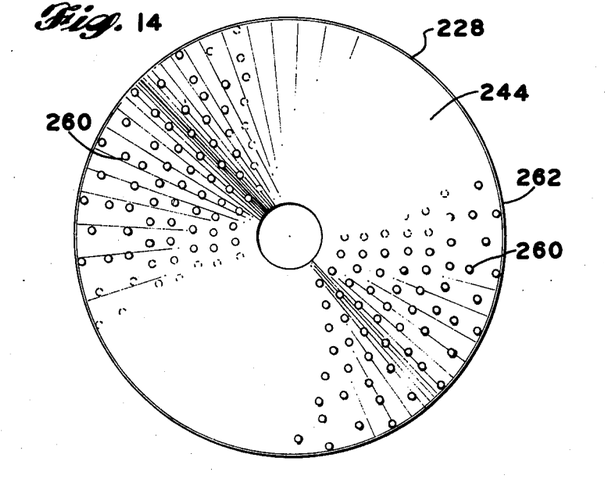
FIG. 14 illustrates an alternate abrasive embodiment for the working face of the prophylactic cup illustrated in FIG. 6.
Figure 15:
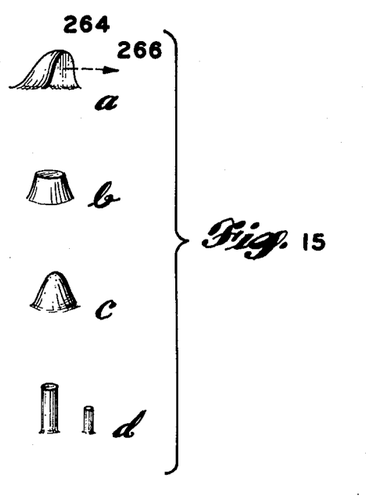
FIG. 15 illustrates four nodular forms which may be employed in the abrasive configuration shown in FIG. 14.

It is also obvious that since bristles are added to the interior surfaces 244 of the prophylactic cup 224 to add an abrasive quality for scrubbing and/or polishing purposes, simply altering the surfaces themselves such as by ribs, can also produce varying degrees of abrasiveness. Thus, FIGS. 14 and 15 illustrate an alternate prophylactic cup embodiment, the interior surfaces 244 of which include a multiplicity of short nodules 260. When the cup is pressed against the dental surface, as with the preferred embodiment, the inherent flexibility of the cup wall, particularly the lower flange, allows the cup to bell out. The resultant cup distortion causes the interior scrubbing surfaces, and particularly the nodules, to engage the dental surface. As the cup is rotated, the nodules, lubricated by dentifrice and saliva, scrub and remove plaque deposits and/or polish the dental surface. The design of the scrubbing nodules is particularly critical, since they must be sufficiently abrasive to break up formations of plaque on the teeth, yet do so without unnecessary abrading the enamel or cementum. The nodules can be extensions of the same material of which the cup itself is comprised and can be formed during the molding of the cup. It is more desirable, however, that the nodules be somewhat harder and less flexible than the body of the cup itself. Ideally, each nodule consists of an inflexible bristle-like unit embedded in the interior surface of the cup by injection molding, as with the previously described bristles in the preferred embodiment. Obviously, nodule length, shape, texture, hardness, angle of attack and pattern or arrangement, as well as cup roational speed and torque, are all factors affecting scrubbing ability. FIG. 14 illustrates the interior of a cup 228 in which the density of nodules 260 decreases toward the outer edge 262. This arrangement is specifically formulated to produce less abrasiveness about the periphery of the cup. Since the peripheral flange enters the gingival crevice and the nodules interface with the relatively soft cementum of the tooth roots, a lower abrasive level is necessary. The lower abrasive level of the working surface engaging the cementum allows the dental hygienic device of the present invention to be safely used by unskilled people.

FIGS. 15a through 15d illustrate several possible nodule forms. That shown in FIG. 15a is asymmetrical and provides what can be described as cutting edges 264 which would address the dental surface as indicated by the arrow 266. For the purposes of this description, however, it shall be assumed that the nodule types illustrated in FIG. 15d are utilized. The possibility of combining these types of nodules with the bristles of the type described in the preferred embodiment should not be overlooked. many nodule/bristle combinations are possible to achieve specialized abrasive configurations. The desired abrasive action may also be provided by abrasive particles embedded in the prophylactic cup inner surface.

In the foregoing description of the prophylactic cup those features which specifically scrub and/or polish the dental surfaces and remove plaque deposits have been described. As previously stated, however, the function of the cup is at least two-fold; cleaning the dental surfaces and massaging and exercising the gingiva. It is this letter objective which shall now be discussed. The previously mentioned smoothly raised crowns 240 on the exterior surfaces of the flexible cup 228, as shown in FIGS. 6, 7, 9 and 10, are responsible for the massaging action achieved by the cup. The crowns 240 are preferably evenly spaced about the periphery of the cup though they need not be to function in the intended manner. Though three crowns are illustrated, the cup may include one, two, three or more, situated at intervals about its exterior surface. While the peripheral flange or rim 250 of the cup is normally 0.1 mm. thick, the crowns 240 are normally 0.25 mm. thick.

Figure 12:
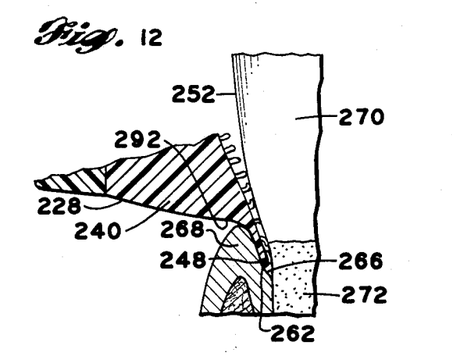
FIGS. 12 and 13 are cross-sectional views of the crown feature of the prophylactic cup shown in FIG. 6 illustrating the manner in which the gingiva is massaged by the crowns.
Figure 13:
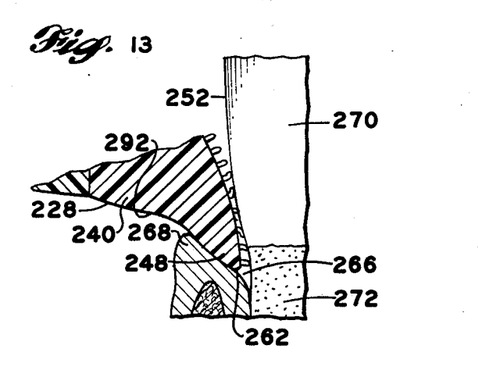

As described earlier in this test, the act of pressing the cup 228 against the tooth surface causes the lower flange 248 to bell out or flair out in a manner corresponding to the contacted tooth surface. With the rotating cup thus applied to the tooth, the belled or flaired out flange 248 can rotate through the gingival crevice 266. The crevice is that space between the free gingiva 268 and the tooth crown 270 and root cementum 272, as illustrated in FIGS. 12 and 13. Flexing and exercising by gently compressing and the allowing relaxing of the gingiva is achieved as successive smoothly contoured crowns or radially outwardly extending eccentric projections 240 on the exterior of the cup peripheral flange rotate through the crevice and alternately displace and relax the gingiva. The cup described in the figures with three crowns 240 on its exterior will flex the gingiva three times during a single revolution of the cup. Another feature of the cup should also be noted. A shoulder 292 is formed on the cup exterior which effectively limits the depth to which the flange 248 may penetrate the gingival crevice 266. The shoulder 292 is situated such that when outer edge 262 penetrates to the maximum desired depth in the crevice, the shoulder encounters the upper extremity of the free gingiva 268 thereby preventing injury along the line of epithelial attachment.

It is also noted that the exterior surface of the cup will physically contact the upper extremity and the inner wall of the gingiva which will lead to keratinization of the contacted gingiva surfaces. This keratinization, or production of a dead outer skin-like layer is believed by some dental authorities to be a valuable occurrence for the prevention of periodontal disease. Accordingly, to prevent abrasion of the keratinization layer, the outer surface of the cup is preferably relatively non-abrasive.

It is obviously desirable to provide an apparatus with interchangeable hygienic heads for each individual using the device. An alternate solution to the completely interchangeable head described in the preferred embodiment is the hygienic sleeve 274 illustrated in FIGS. 16 and 17. The sleeve comprises a prophylactic cup 224 molded on a tubular fitting 276 possessing splines 278 which prevents the cup 224 from rotating on the fitting 276. The fitting 276 is also annularly grooved 280 such that the fitting is rotatably retained in a small opening in the closed end of the flexible plastic sleeve 282. Thus, via the fitting 276, the hygienic sleeve 274 rotatably mounts the prophylactic cup 224 for use.

Figures 16, 17:
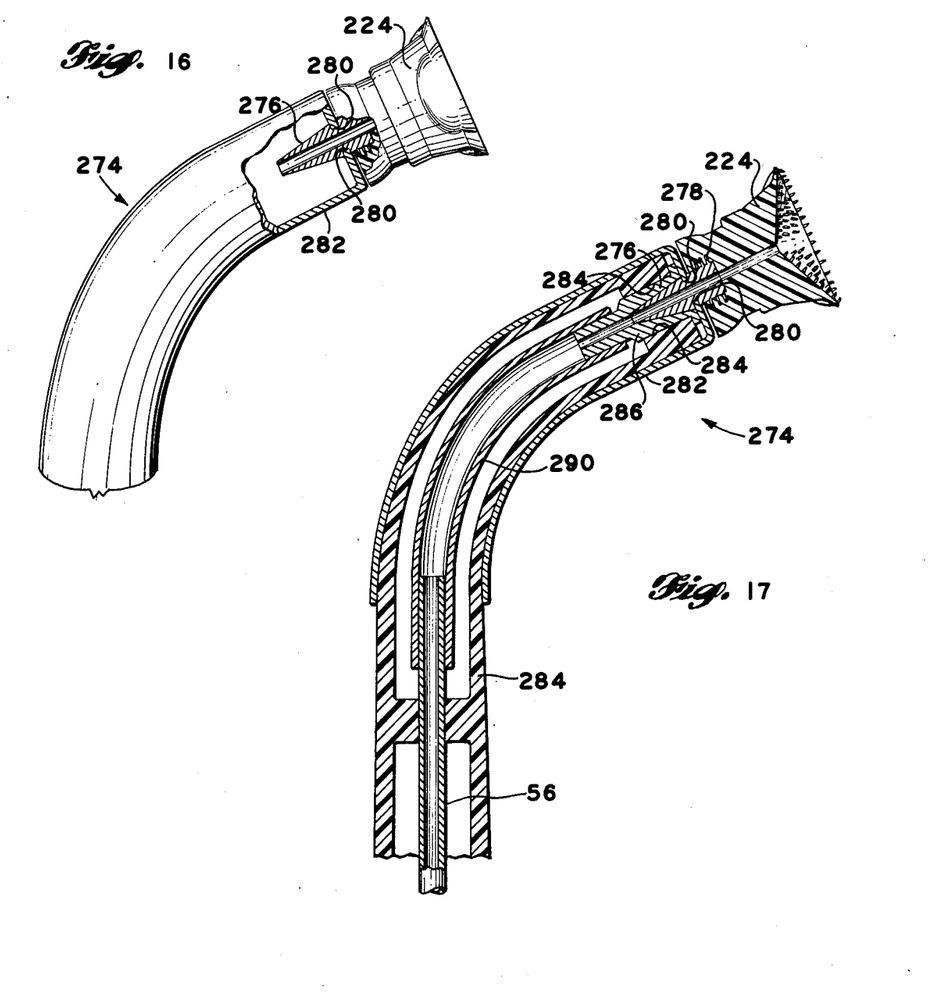
FIG. 16 is a partially cutaway view of removable hygienic sleeve assembly which may be used with alternate embodiments of the dental hygiene instruments shown in FIGS. 1 through 4A.
FIG. 17 is a cross-section view of the hygienic sleeve shown in FIG. 16.

FIG. 17 illustrates the hygienic sleeve 274 installed on the operating stem 284 of the device. Note that the sleeve 282 is installed over the stem 284 and is pushed on until the prophylactic cup fitting 276 positively engages the tapered channel in collar 286. The collar 286 is rotatably mounted in the end of the stem 284 within bearing surfaces 288. The collar 286 is interconnected with drive 56 (references FIGS. 1 and 2) by a flexible plastic or rubber shaft segment 290. The flexible segment 290 couples rotational drive from the shaft 56 to the collar 286 and subsequently to the prophylactic cup 244 through the frictional coupling between the collar 286 and fitting 276. Thus, there is formed a flexible angular drive chain, and since all shaft segments and the collar 286 and fitting 276 enclose hollow cores, a dentifrice channel is provided for the prophylactic cup 224.

The dentifrice use with the dental hygiene instrument described herein is specially formulated to provide necessary cleaning qualities and to meet obvious lubrication requirements. A non-abrasive dentifrice is contemplated, however, certain conditions might require the use of certain relatively low abrasive compounds or the like. The more technical, physical and chemical properties of a product of this nature must be achieved in refined proportion, while combining the accepted properties of conventional dentifrices and other oral hygienic products such as color, flavor, foaming action, feel, and physical appearance.

The formulation for a dentifrice meeting these requirements is typically based on a solution of water and/or lubricant base such as glycerin and/or propylene glycol. Alcohols such as ethanol and/or i-propylalcohol may be added to the basic formulation in small amounts to improve product clarity, and solubility of certain surfactants and flavors. The alcohol also prevents low temperature clouding and improves product flavor by countering the sweet taste of glycerin and imparting a fresh after taste. The beneficial abrasive action of many compounds is well known in conventional dentifrices, however, excess abrasive action would be harmful in a dentifrice used with the device of the present invention. Many anti-plaque/anti-caries agents are available which can be used in this formulation; sodium monofluorophosphate being one well suited.

Thickening agents are added to this dentifrice formulation to hold whatever abrasive agent which might be incorporated in suspension and to produce a product with physical appearances and properties similar to conventional dentifrices. Many thickening agents are available including fumed silica and methylcellulose which are generally suited to this application. Flavoring and coloring agents of types commercially produced for use with conventional dentifrices are also added. A surfactant such as sodium lauryl sulfate could also be included to increase the solubility of the coloring and flavoring agents and to impart foaming properties to the final product.

A final formulation for a dentifrice which meets the unique requirements of the previously described dental hygienic device could involve the components listed below. Possible concentration range is given and probable ratio is indicated in parenthesis.

| 1. | Water | 5–98% (97.1) |
|---|---|---|
| 2. | Lubricating agents such as Vegetable Oil, Glycerin, Propylene Glycol | 0–95% (0) |
| 3. | Alcohol | 0–20% (0) |
| 4. | Fluorides such as Sodium Fluoride | 0.1–2% (1) |
| 5. | Surfactant such as Sodium Lauryl Sulfate | 0–2% (0.5) |
| 6. | Thickening Agents | 0–2% (.5) |
| 7. | Flavor | 0–2% (0.8) |
| 8. | Coloring Agent | 0–1% (0.1) |

Although the preferred embodiments have been described with a certain degree of particularity it is understood that the descriptions are by way of example only and that various modifications and combinations and rearrangements of the parts are possible within the scope and the spirit of the invention as hereinafter claimed.

I claim:
1. A dental hygienic device including a rotable bell-shaped prophylactic cup and means for rotating said cup about the axis thereof, said cup having a generally concave inner working surface designed to flair outwardly and adapt to contacted tooth surfaces, said inner working surface having a circumferentially outer lip for insertion into the gingival crevice, the outer surface of said cup including a shoulder for limiting the insertion of said lip into the gingival crevice, said inner working surface having abrasive means thereon, said abrasive means being arranged to have a varying abrasive effect dependent upon the radial distance from the outer circumference of said lip, the abrasive means having a lesser abrasive effect on that portion of the inner working surface immediately adjacent said outer lip than on other portions of the inner working surface.

2. The dental hygienic device of claim 1 wherein said means to apply a rotary motion includes a hand held casing containing a motor and a gear train.

3. The dental hygienic device of claim 1 wherein said abrasive means include protrusions extending from said inner working surface.

4. The dental hygienic device of claim 3 wherein said protrusions extend substantially perpendicularly from said inner surface.

5. The dental hygienic device of claim 1 wherein said abrasive means includes abrasive particles embedded in the inner working surface of said cup.

6. The dental hygienic device of claim 1 wherein the outer surface of said cup is substantially smooth and non-abrasive compared to the inner working surface.

7. A dental hygienic device including a rotable bell-shaped prophylactic cup and means for rotating said cup about the axis thereof, said cup having a generally concave inner working surface designed to flair outwardly and adapt to contacted tooth surfaces, said inner working surface having a circumferentially outer lip for insertion into the gingival crevice, the outer surface of said cup including a shoulder for limiting the insertion of said lip into the gingival crevice, said inner working surface including abrading protrusions extending therefrom, said protrusions adjacent the central area of said inner working surface being less flexible than the protrusions on that portion of the inner surface insertable into the gingival crevice.

8. A dental hygienic device including a rotable bell-shaped prophylactic cup and means for rotating said cup about the axis thereof, said cup having a generally concave inner working surface designed to flair outwardly and adapt to contacted tooth surfaces, said inner working surface having a circumferentially outer lip for insertion into the gingival crevice, the outer surface of said cup including means for limiting the insertions of said lip into the gingival crevice, said inner working surface having abrasive means thereon, said abrasive means being arranged to have a varying abrasive effect dependent upon the radial distance from the outer circumference of said lip, the abrasive means having a lesser abrasive effect on that portion of the inner working surface insertable into the gingival crevice than on other portions of the inner working surface, said outer surface further including at least one radially outwardly extending portion eccentric to the remainder of the outer surface with respect to the rotational axis of said cup for applying a compressive and then a relaxive force to gum tissues simultaneously with said inner working surface abrading contacted tooth surfaces.

9. The device of claim 8 wherein said portion extends smoothly from said outer surface.

10. The device of claim 9 wherein said other portion of said inner working surface includes a plurality of second abrasive means for polishing contacted tooth surfaces.

11. A dental hygienic device for use with a relatively non-abrasive dentifrice to remove dental plaque from tooth surface and to stimulate the free gingiva, said device including a rotatable, generally bell-shaped prophylactic cup having a generally concave inner working surface and a relatively non-abrasive outer surface, said outer surface having at least one smoothly, outwardly extending portion eccentric to the remainder of the outer surface for applying a compressive and then a relaxive force to the free gingiva, said cup being relatively flexible away from its axis rotation to flair outwardly and adapt to contacted tooth surfaces, said cup having a relatively thinner outer periphery for entry into the gingival crevice and a relatively thicker portion adjacent to the thinner portion which is incapable of entry into the gingival crevice, said inner working surface having abrasive means selectively arranged thereon, said abrasive means being arranged on said inner surface such that the portion of the inner surface at the thinner outer periphery of the cup has a lower abrasive effect than other portions of the inner working surface.

* * * * *